May 9, 1972 P. ECKE Plant Pat. 3,160
POINSETTIA PLANT
Filed July 24, 1970
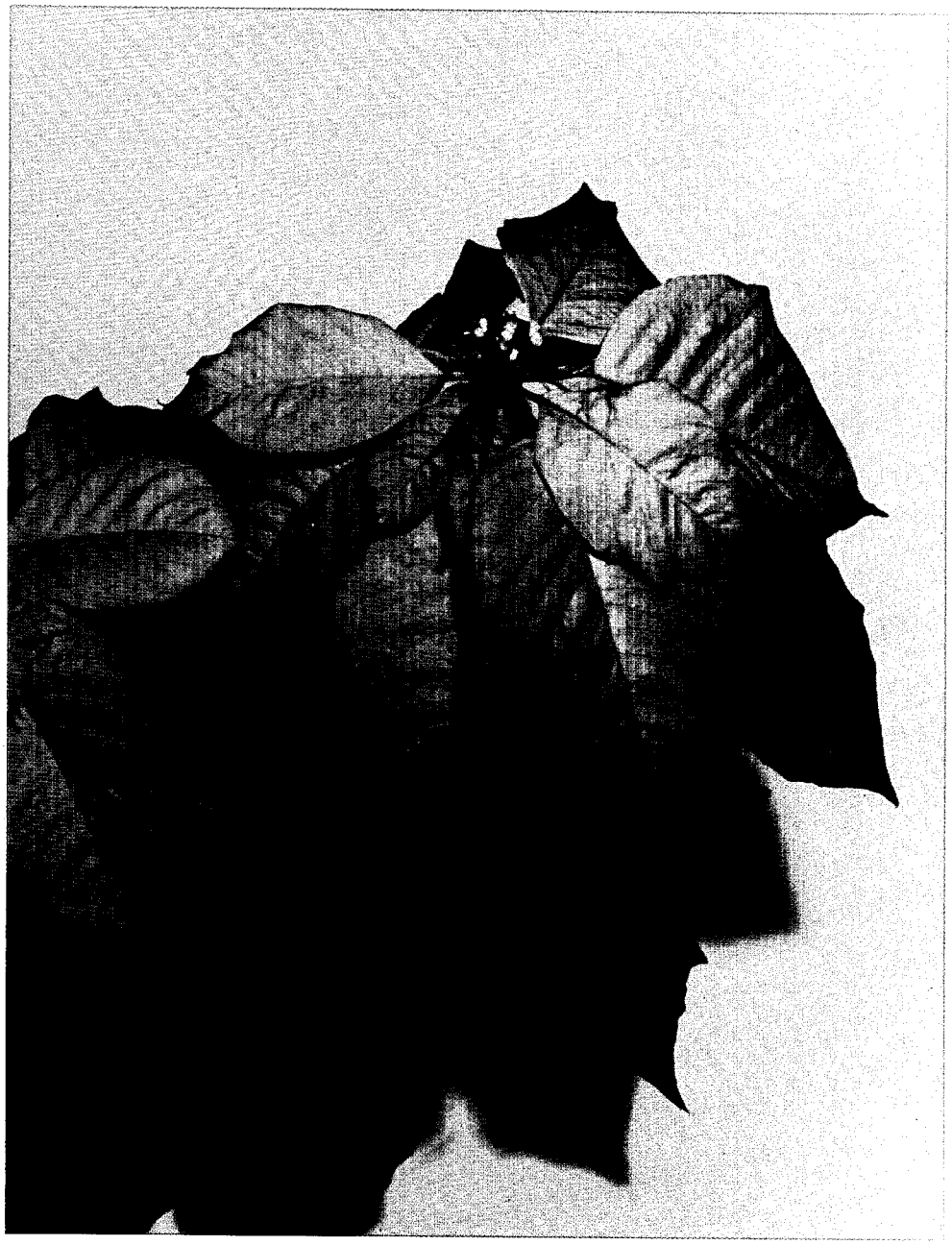
Inventor
Paul Ecke
By: Robb & Robb
Attorneys

United States Patent Office

Plant Pat. 3,160
Patented May 9, 1972

3,160

POINSETTIA PLANT

Paul Ecke, Encinitas, Calif., assignor to Paul Ecke, Inc., Encinitas, Calif.

Filed July 24, 1970, Ser. No. 58,210
Int. Cl. A01h *5/00*
U.S. Cl. Plt.—86 1 Claim

The present invention relates to a new and distinct variety of poinsetta plant (botanically known as *Euphorbia pulcherrima*) which was discovered by me as a dark red cultivated sport of the red poinsettia variety known as "Annette Hegg" (Plant Patent No. 2,962), said discovery having been made by me in one of my greenhouses located at Encinitas, Calif.

At the time of my discovery aforesaid, I was growing in my greenhouses at Encinitas various poinsettia varieties, including many plants of the patented variety known as "Annette Hegg." In the course of these growing operations, my attention was attracted to one particular plant among those of "Annette Hegg" which bore bracts of a substantially darker red color than the normal red bracts of "Annette Hegg." Close inspection of this particular plant showed that it had sported, so I carefully preserved the sport and kept it under close observation. In due course, I asexually reproduced the sport by vegetative cuttings taken therefrom and planted in my greenhouses at Encinitas. Continued observations and tests of the original sport and its progeny derived from the vegetative cuttings aforesaid and which have been propagated successfully through several generations, fully confirmed that the dark red bracks come true and remain very stable. While my observations and tests have shown that for all practical purposes, the new sport generally resembles the parent variety "Annette Hegg" except for its darker red bract color, I have also found that the darker red bract color of the sport retains its brilliance much longer when the plants are grown in the home after removal from the greenhouse, than the bracks of "Annette Hegg" which tend to fade rather quickly. Also, the bracts of the sport do not droop as much as those of "Annette Hegg" when the plants reach maturity. Another significant distinction is that the leaf petioles of my new sport are red on both the top and bottom surfaces of the petioles.

The various characteristics and distinctions referred to above represent a unique and commercially valuable combination of features which distinguish the sport from its parent variety, as well as from all other poinsettia varieties of which I am aware, as evidenced by the following summary of characteristics which are outstanding in this new sport:

(1) A short-growing and compact plant habit;
(2) A uniform and fast rooting habit;
(3) A self-branching habit resulting in the production of multiple blooms without pinching off the terminal buds as required for other poinsettia varieties;
(4) Attractive green foliage which is usually somewhat darker green in color than the foliage of "Annette Hegg," with the leaves having distinctive petioles of red color on both the upper and lower surfaces thereof;
(5) Attractive, darker red bracts than the normal red bracts of "Annette Hegg," said dark red bracts having less tendency to droop than the bracts of "Annette Hegg" when the plants reach maturity, and the darker red color of the bracts being more stable and retaining its brilliance much longer when the plants are used for home decoration; and
(6) Long-lasting plant qualities.

The accompanying drawing shows a typical specimen plant of my new poinsettia variety as depicted in color as nearly true as it is reasonably possible to make the same in a color illustration of this character.

Although the details of my new poinsettia sport, except for the principal differences referred to in the foregoing, are generally similar to those described in Plant Patent No. 2,962, to which reference may be readily had, the following brief description is given for convenience, with color terminology in accordance with Wilson's Horticultural Colour Chart, except where general color terms of ordinary dictionary significance are obvious:

Parentage: Sport of "Annette Hegg" (Plant Patent No. 2,962).
Propagation: Holds its distinguishing characteristics through succeeding propagations by vegetative cuttings.
Form: Short-growing; compact.
Habit of growth: Self-branching; does not require pinching to produce multiple blooms.
Rooting habit: Very uniform and very fast.
Blooming habit: 9-week variety.
Blooming season: Blooms predictably and in time for Christmas season and beyond; also good for flowering in spring, summer and autumn.
Foliage:
*Shape.*—Similar to "Annette Hegg."
*Color.*—Usually somewhat darker green than foliage of "Annette Hegg," with leaf petioles of red color on both upper and lower surfaces. New foliage—upper side—Spinach Green, Plate 0960—lower side—Spinach Green, Plate 0960—old foliage—upper side—Ivy Green, Plate 0001060—lower side—Ivy Green, Plate 0001060/2.
Bracts: Obovate; relatively broad; retains brilliance longer and less drooping when mature than bracts of "Annette Hegg." Color—Near Cardinal Red, Plate 822/1; substantially darker red color than bracts of "Annette Hegg."
Flowers (Cyathia): Early; numerous; strong; little if any tendency to split; do not drop off prematurely.
Reproductive organs:
*Stamens.*—Quite numerous; from about ⅛ inch to ¼ inch long. Color—Near Currant Red, Plate 821/2.
*Pollen.*—Strong. Color—Near Canary Yellow, Plate 2.
*Styles.*—Color—Near Currant Red, Plate 821/2.
*Ovaries.*—Color—Near Scheele's Green, Plate 860.
*Nectar cups.*—Color—Near Buttercup Yellow, Plate 5/1.

General observations: While this new sport generally resembles the variety "Annette Hegg," it principally distinguished therefrom by its somewhat darker green foliage color, with leaf petioles which are red on both their upper and lower surfaces; darker red bracts which retain their brilliance much longer and with less tendency to fade when grown under the same conditions as "Annette Hegg;" and less tendency of the bracts to droop when the plants reach maturity.

I claim:

1. A new and distinct variety of poinsettia plant, substantially as herein shown and described, characterized particularly as to novelty by the unique combination of a short-growing and compact plant habit, a uniform and fast rooting habit, a self-branching habit resulting in the production of multiple blooms without pinching off the terminal buds as required for other poinsettia varieties, attractive green foliage which is usually somewhat darker green in color than the foliage of "Annette Hegg," with the leaves having distinctive petioles of red color on both the upper and lower surfaces thereof, attractive, darker red bracts than the normal red bracts of "Annette Hegg," said dark red bracts having less tendency to droop than the bracts of "Annette Hegg" when the plants reach maturity, and the darker red color of the bracts being more stable and retaining its brilliance much longer when the plants are used for home decoration, and long-lasting plant qualities.

No references cited.

ROBERT E. BAGWILL, Primary Examiner